US00PP37675P3

(12) United States Plant Patent
Koot

(10) Patent No.: US PP37,675 P3
(45) Date of Patent: Sep. 8, 2026

(54) ***BUDDLEJA* PLANT NAMED 'Botex 014'**

(50) Latin Name: *Buddleja davidii*
Varietal Denomination: Botex 014

(71) Applicant: Johannes Adrianus Maria Koot, Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 19/330,792

(22) Filed: Sep. 16, 2025

(65) Prior Publication Data

US 2026/0090489 P1 Mar. 26, 2026

(30) Foreign Application Priority Data

Sep. 25, 2024 (QZ) ..... 20242105

(51) Int. Cl.
*A01H 5/02* (2018.01)
*A01H 6/00* (2018.01)

(52) U.S. Cl.
USPC ..... Plt./242
CPC ..... *A01H 6/00* (2018.05); *A01H 5/02* (2013.01)

(58) Field of Classification Search
USPC ..... Plt./242
CPC ..... A01H 5/02; A01H 5/00; A01H 6/00
See application file for complete search history.

(56) References Cited

PUBLICATIONS

AIPH Record Number of New Plants Set to Shine at Plantarium Groen-Direkt 2025 Flora Culture International, retrieved on Dec. 3, 2025 at https://aiph.org/floraculture/news/record-number-of-new-plants-set-to-shine-at-plantariumgroen-direkt-2025/, 15 pp. (Year: 2025).*

Facebook Manor Farm Shops and Garden Centre Post 2024, retrieved on Dec. 3, 2025 at https://www.facebook.com/manorfarmshopsleasingham/posts/beautiful-buddleja-butterfly-candy-little-cerise-compact-habit-ideal-for-patio-p/951798390085336/, 2 pp. (Year: 2024).*

Kordes Jungpflanzen Buddleja davidii Butterfly Candy Little Bubblegum (Botex014), retrieved on Dec. 3, 2025 at https://www.koju.de/en/BUDDLEJA-davidii-Butterfly-Candy-Little-Bubblegum-BOTEX014/10299, one page (Year: 2025).*

Plumridge Nurseries Buddleja Butterfly Candy Little Bubblegum P9 2024, retrieved on Dec. 3, 2025 at https://www.plumridgenurseries.co.uk/product/buddleja-butterfly-candy-little-bubblegum-p9, 3 pp. (Year: 2024).*

* cited by examiner

*Primary Examiner* — June Hwu
(74) *Attorney, Agent, or Firm* — Penny J. Aguirre

(57) ABSTRACT

A new cultivar of *Buddleja* plant named 'Botex 014' that is characterized by its dense and very compact plant habit with upright stems, its flowers that are vibrant neon pink in color, its neat and naturally round plant shape, its very floriferous blooming habit, and its flowers that have a sweet fragrance.

2 Drawing Sheets

Botanical classification: *Buddleja davidii.*
Variety denomination: 'Botex 014'.

CROSS-REFERENCE TO A RELATED APPLICATION

This application claims priority to European Community Plant Variety Office (CPVO) Plant Breeder's Rights Application No. 2024/2105 filed on Sep. 25, 2024, under 35 U.S.C. 119(f), the entire contents of which is incorporated by reference herein. The Applicant received the information for the Plant Breeder's Rights Application directly from the Inventor.

BACKGROUND OF THE INVENTION

The present invention relates to a new and distinct cultivar of *Buddleja davidii* and will be referred to hereafter by its cultivar name, 'Botex 014'. 'Botex 014' is a new shrub grown for use as an ornamental landscape plant.

The new cultivar of *Buddleja* is a selection from an ongoing breeding program conducted by the Inventor in Kaatsheuvel, The Netherlands with the goal of creating new cultivars of *Buddleja* with very neat, well-branched, and compact plant habits combined with unique flower colors and floriferous blooming habits.

The Inventor made a cross in July of 2020 between an unnamed and unpatented proprietary plants in the Inventor's breeding program as both the female and male parents. The Inventor selected 'Botex 014' in July of 2022 as a single unique plant amongst the seedlings that resulted from the above cross.

Asexual propagation of the new cultivar was first accomplished by the Inventor using stem cuttings in Kaatsheuvel, The Netherlands in 2022. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 014' as a unique cultivar of *Buddleja.*

1. 'Botex 014' exhibits a dense and very compact plant habit with upright stems.
2. 'Botex 014' exhibits flowers that are vibrant neon pink in color.
3. 'Botex 014' exhibits a neat and naturally round plant shape.
4. 'Botex 014' exhibits a very floriferous blooming habit.
5. 'Botex 014' exhibits flowers that have a sweet fragrance.

Both the female and male parent differs from 'Botex 014' in having flowers that are lighter and less bright pink in color. 'Botex 014' can be compared to the *Buddleja* cultivars 'Attraction' (not patented) and 'Royal Red' (not patented). 'Attraction' differs from 'Botex 014' in having a much taller plant height, a less compact plant habit, and flowers that are more purple in color and less vibrant. 'Royal Red' differs from 'Botex 014' in having a much taller plant height, a less compact plant habit, and flowers that are more purple in color and less vibrant, and inflorescences that are longer and larger in size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include websites listing by Plantipp (the breeder's representative), plantariumgroenderdkt (instagram), Shop Plant Factory, Visions Pictures, Franciscus van de Weil (facebook), Vitaflora, Young Plants Holland, Zahradictvo Rool, Plantago, Floral Daily, e-katalogroslin, Zahradnictvi Spomysl, Kerteszet Rool, Feur NV, Leenders Plats, FloraXchange, Baldur, The *Buddleja* Garden, Specialmix, J. Parkers, and Flowerwood Nursery.

BRIEF DESCRIPTION OF THE DRAWINGS

The accompanying color photographs illustrate the overall appearance and distinct characteristics of the new *Buddleja*. The photographs were taken of a one-year-old plant as grown in a greenhouse in a 21-cm container in Kaatsheuvel, The Netherlands.

The photograph in FIG. 1 provides a side view of the plant habit of 'Botex 014' in bloom.

Figure 1:
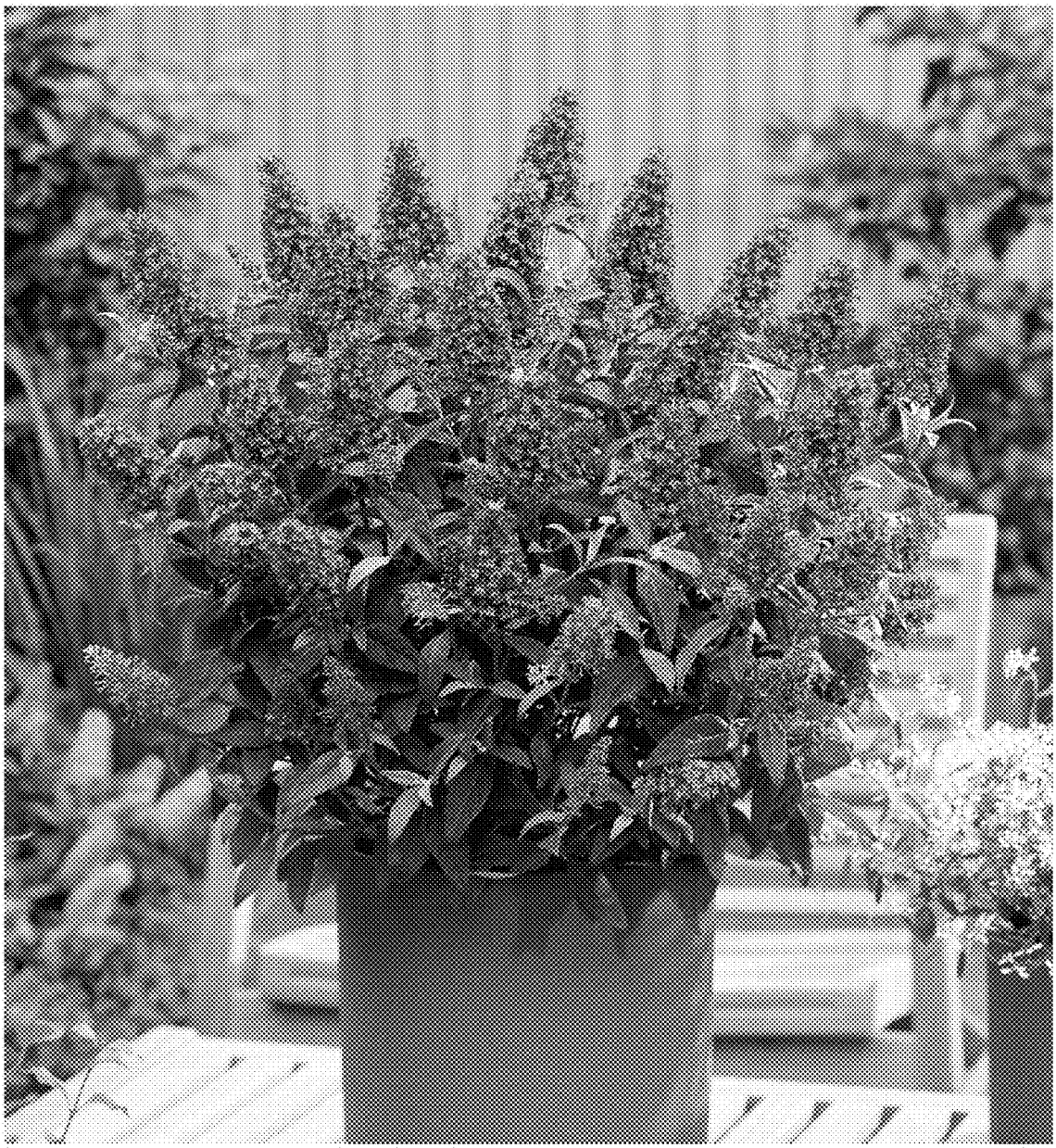
Figure 2:
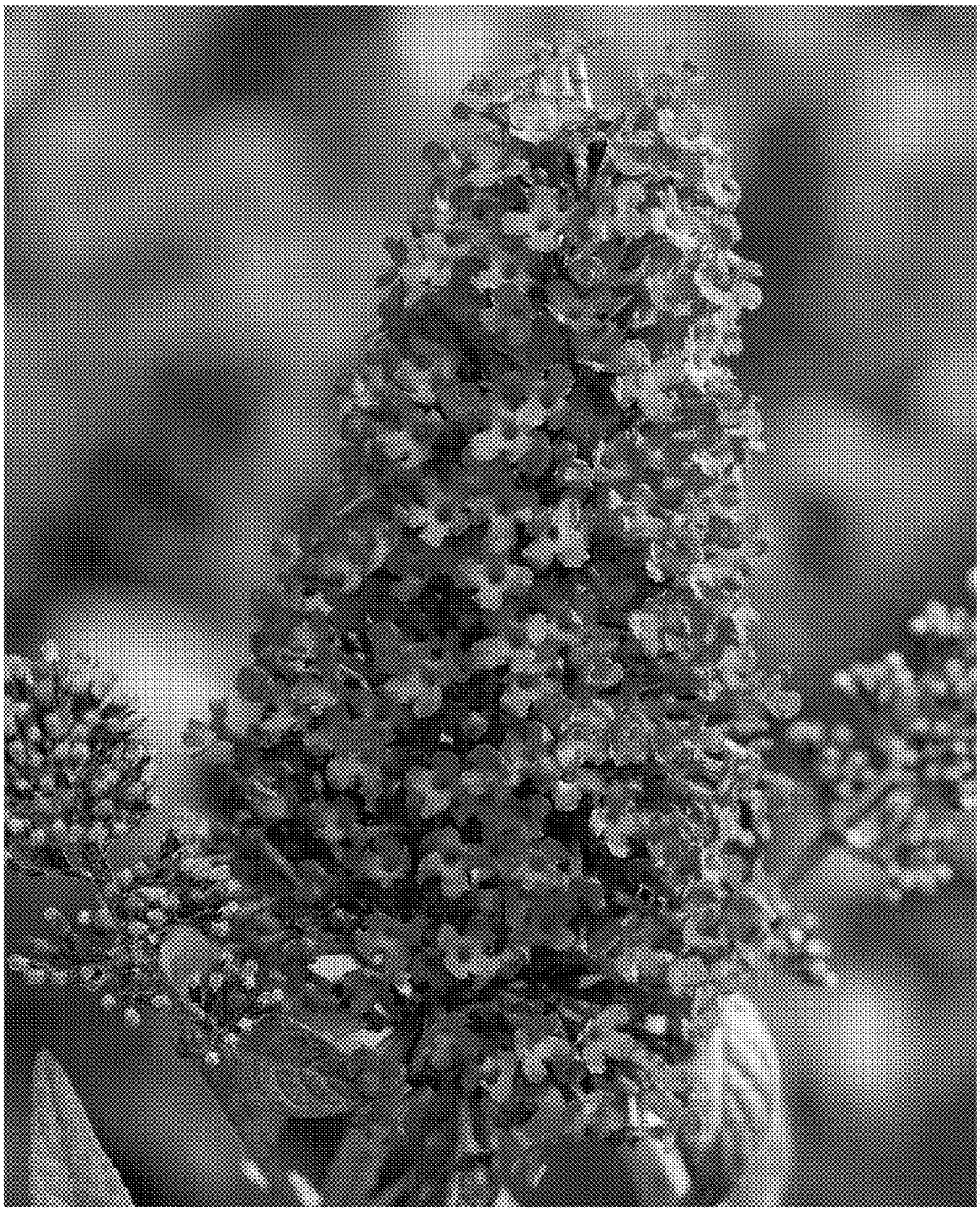

The photograph in FIG. 2 provides a close-up view of an inflorescence of 'Botex 014'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 21-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Begins in mid July and blooms into October in The Netherlands.

*Plant type*.—Deciduous perennial shrub.

*Plant habit*.—Compact, upright stems with rounded shape, densely branched.

*Plant size*.—An average of 36 cm in height, 37 cm in width as a one-year-old plant grown in a container, reaches 80 to 90 cm in height and an average of 80 cm in width as grown in the landscape.

*Cold hardiness*.—At least to U.S.D.A. Zone 5.

*Diseases and pests*.—No susceptibility and resistance to diseases or pests has been observed.

*Propagation*.—Stem cuttings.

*Root description*.—Fibrous.

*Root development*.—An average of 5 weeks to initiate roots and e7 weeks to fully root as a young plant in a P9 container.

*Growth rate*.—Vigorous.

Branch description:

*Branch shape*.—Quadrangular.

*Branch color*.—Young stems; 145A to 145B, mature stems; 144B with a layer of N187A, old wood 199A to 199B.

*Branch strength*.—Strong.

*Branch size*.—An average of 25 cm in length and 5 mm in diameter.

*Branch surface*.—Medium pubescence.

*Branch aspect*.—Held in multiple angles.

*Branch internode length*.—Average of 4 cm.

*Branching*.—2 main branch, 3 secondary branches per main branch, 6 tertiary per secondary branch.

Foliage description:

*Leaf shape*.—Narrowly elliptical to elliptical.

*Leaf division*.—Simple.

*Leaf base*.—Attenuate.

*Leaf apex*.—Acute.

*Leaf fragrance*.—None.

*Leaf venation*.—Pinnate, both surfaces match leaf surfaces; mature leaves 137A on upper surface and 191B on lower surface.

*Leaf margins*.—Serrate.

*Leaf arrangement*.—Opposite.

*Leaf attachment*.—Petiolate.

*Leaf surface*.—Both sides are smooth, matte, and pubescent with medium leaf bulging between veins.

*Leaf size*.—An average of 8 cm in length and 3 cm in width.

*Leaf quantity*.—10 per stem.

*Leaf color*.—Young upper surface; 137C, base 138B, young lower surface; 191C, mature upper surface; 137A, mature lower surface; 191B.

*Petioles*.—An average of 2 mm in length and diameter, medium to high strength, both surfaces 145B in color, both surfaces slightly pubescent.

Inflorescence description:

*Inflorescence type*.—Compound terminal and axial panicles, cylindrical in shape.

*Inflorescence size*.—Up to 7.5 cm in height and 4.5 cm in width.

*Flower fragrance*.—Sweet, pleasant and medium in strength.

*Lastingness of flowers*.—An average of 5 days, persistent, inflorescence is semi-indeterminate.

*Flower buds*.—Oblong, average of 6 mm in length and 1 mm in diameter, 67A and 145C in color.

*Flower aspect*.—Upright.

*Flower quantity*.—An average of 200 flowers per inflorescence.

*Flower density*.—Dense.

*Flower type*.—Single, salverform.

*Flower surface*.—All surfaces glabrous and smooth.

*Flower size*.—An average of 1 cm in height, 6 mm in diameter, flower throat; 4 mm in length, 1 mm in diameter, flower tube; 5 mm in length, 1 mm in diameter.

*Peduncles*.—An average of 1.5 cm in length and 2 mm in diameter, 145A in color, strong, glossy and pubescent surface.

*Pedicels*.—An average of 2 mm in length and 1 mm in diameter, 145A in color, strong, glossy and pubescent surface.

*Calyx*.—Campanulate in shape, an average of 2 mm in depth and 1.5 mm in diameter.

*Sepals*.—4, 1 whorl, rotate arrangement, fused into a campanulate shape, 2 mm in length, 1 mm in width, lanceolate in shape, acute apex, fused base, entire margin, both surfaces are matte and slightly pubescent, color when opening and fully open upper and lower surface; 145A and N187A.

*Petals*.—4 to 5, rotate, fused into salverform, 1 whorl, roughly spathulate in shape, slightly undulate margins, rounded apex, an average of 3 mm in length and width, outer and inner surface is glabrous, velvety and matte, color: upper surface when opening and fully open; young upper and lower surface N66A and 67A, mature upper and lower surface 67A to 67B, inside tube and throat 25A, outer surface of tube 67A, outside of throat 67B, with a hint of 25B.

Reproductive organs:

*Gynoecium*.—1 pistil, 2 mm in length, style; an average of 1.5 mm in length, 145D in color, stigma; elongated, 1 mm in length and 145B in color, ovary 145D in color.

*Androecium*.—Stamens; 4, filament; 3 mm in length, transparent, anther; ovate in shape, 1 mm in length, 11D in color, pollen; low in quantity, 11D in color.

*Fruit and seed*.—No seeds or fruit have been observed to date.

It is claimed:

1. A new and distinct cultivar of *Buddleja* plant named 'Botex 014' as herein illustrated and described.

* * * * *